United States Patent [19]

Murakami et al.

[11] Patent Number: 5,250,423
[45] Date of Patent: Oct. 5, 1993

[54] METHOD FOR THE PRODUCTION OF L-LYSINE EMPLOYING THERMOPHILIC CORYNEBACTERIUM THERMOAMINOGENES

[75] Inventors: Yutaka Murakami; Harufumi Miwa; Shigeru Nakamori, all of Kawasaki, Japan

[73] Assignee: Ajinomoto Co., Inc., Tokyo, Japan

[21] Appl. No.: 688,301

[22] Filed: Apr. 22, 1991

[30] Foreign Application Priority Data

Apr. 20, 1990 [JP] Japan ................................. 2-104459

[51] Int. Cl.$^5$ ............................................. C12P 13/08
[52] U.S. Cl. .................................. 435/115; 435/252.1; 435/843
[58] Field of Search ................... 435/115, 252.1, 843

[56] References Cited

U.S. PATENT DOCUMENTS

| | | | |
|---|---|---|---|
| 3,959,075 | 5/1976 | Inuzuka et al. | 435/843 |
| 4,169,763 | 10/1979 | Nakayama et al. | 435/843 |
| 4,275,157 | 6/1981 | Tosaka et al. | 435/843 |
| 4,560,654 | 12/1985 | Miwa et al. | 435/843 |
| 4,657,860 | 4/1987 | Nakanishi et al. | 435/843 |
| 4,980,285 | 12/1990 | Sano et al. | 435/115 |

FOREIGN PATENT DOCUMENTS

| | | | |
|---|---|---|---|
| 2509748 | 1/1983 | France | 435/115 |
| 2612937 | 9/1988 | France | |
| 0026391 | 3/1978 | Japan | 435/115 |
| 2042995 | 2/1990 | Japan | 435/115 |
| 0851231 | 8/1985 | Rep. of Korea | |

OTHER PUBLICATIONS

Tasaka et al., "L-Lysine", In: Biotechnology of Amino Acid Producton, Aida et al. (eds) pp. 152–172, 1986.

*Primary Examiner*—Marian C. Knode
*Attorney, Agent, or Firm*—Oblon, Spivak, McClelland, Maier & Neustadt

[57] ABSTRACT

L-lysine is produced by culturing, in a medium, an L-lysine-producing mutant which belongs to the genus *Corynebacterium thermoaminogenes* which is capable of growing at 40° C. or higher and which has resistance to S-(2-aminoethyl)-L-cysteine thereby producing and accumulating L-lysine in the culture medium, and collecting L-lysine from the culture medium.

5 Claims, No Drawings

5,250,423

METHOD FOR THE PRODUCTION OF L-LYSINE EMPLOYING THERMOPHILIC CORYNEBACTERIUM THERMOAMINOGENES

BACKGROUND OF THE INVENTION

1. Field of the Invention

The present invention relates to a method for producing L-lysine by fermentation and to an L-lysine producing mutant.

2. Description of the Background

L-lysine, which is important as an additive for livestock feed, and the like has been mainly prepared by fermentation.

In the industrial preparation of L-lysine by fermentation, some technical factors must be considered in order to achieve economic improvement of the process. These factors include, for example, improvements in yield based on sugar, improvements in concentration of L-lysine which accumulates, shortening of culturing time, and the like.

In culturing, it is important to elevate the temperature for culturing. Culturing is generally carried out at an optimum temperature for L-lysine fermentation. Where conventional L-lysine-producing bacteria are used, the temperature is generally between 28° and 35° C. When culturing begins, the heat of fermentation is generated so that when the system is allowed to stand, the temperature of the culture medium increases with the result that the amount of L-lysine which forms seriously decreases. In order to maintain the temperature of the culture medium in the optimum range, it is necessary to mount a heat exchanger in the fermentation tank and cyclize cool water into the tank. In order to obtain cool water, a cooler must be used. However, since the heat of fermentation generated is very large, the amount of electric energy consumed by the cooler is very large. Accordingly, if the culture temperature for fermentation of L-lysine is increased, the cooling load decreases so that economy of L-lysine production in an industrial scale can be improved.

The method described in Korean Patent Publication No. 85-231 (published August 23, 1985) proposes to increase the culture temperature in the fermentation of L-lysine. That is, the method disclosed employs the L-lysine-producing variant TR-3579 (KFCC 10065) which belongs to the genus *Corynebacterium*, which has resistance to a lysine analogue and resistance to temperature and further requires homoserine, leucine and valine in combination. Culturing of the variant occurs in a medium at a high temperature (37° to 45° C), thereby producing and accumulating L-lysine in the culture medium.

Since the L-lysine-producing variant used in this method is obtained by improving conventional L-lysine-producing bacteria (grown at 30° to 35° C.) by a mutation which results in the production of L-lysine at a high temperature (37° to 45° C.). the variant has complex auxotrophy of homoserine, leucine and valine as described above, because of the several step mutation employed. Therefore, this method is not practical.

Japanese Patent Application Laid-Open No. 58-170487 discloses a method for producing L-lysine by fermentation which comprises culturing a mutant belonging to the genus Corynebacterium, having a reduced pyruvate kinase acivity, which is capable of producing L-lysine and also which has optional resistance to S-(2-aminoethyl)-L-cysteine in a medium thereby producing and accumulating L-lysine in the culture broth and then collecting L-lysine.

The temperature for fermentation in the method is set at 20° to 40° C., but as is assumed from the only working example (Example 1) in the reference where a temperature of 30° C. is adopted, the growth of the bacteria used is not significant at about 40° C. which is the upper limit of the temperature range for fermentation. Marked formation and accumulation of L-lysine are not observed either. This has been confirmed by experimentation. A need therefore continues to exist for an improved method of producing L-lysine by fermentation.

SUMMARY OF THE INVENTION

Accordingly, one object of the present invention is to provide bacteria which are capable of producing L-lysine by fermentation at a high temperature which can withstand practical use conditions.

Another object of the present invention is to provide a method for producing L-lysine by fermentation under practical conditions at a high temperature.

Briefly, these objects and other objects of the invention as hereinafter will become apparent can be attained in a method for producing L-lysine by fermentation which comprises culturing, in a medium, an L-lysine-producing mutant belonging to the genus Corynebacterium which is capable of growing even at 40° C. or higher and which has a resistance to S-(2-aminoethyl)-L-cysteine thereby producing and accumulating L-lysine in the culture medium and collecting L-lysine from the culture medium.

The invention also provides an L-lysine-producing mutant per se which can be advantageously utilized in the method described above for producing L-lysine by fermentation.

DETAILED DESCRIPTION OF THE PREFERRED EMBODIMENTS

As a result of extensive investigations it has now been found that by using a mutant modified into L-lysine-producing bacteria by imparting AEC resistance to thermophilic bacteria belonging to the genus Corynebacterium which are capable of growing at 40° C. or higher, the objectives described above can be achieved. Based on this finding, the present invention has been accomplished.

The L-lysine-producing mutant of the invention which belongs to the genus Corynebacterium is capable of growing at 40° C. or higher and has AEC resistance. It is obtained by subjecting bacteria belonging to the genus Corynebacterium which are capable of growing at 40° C. or higher, such as for example, L-glutamic acid-producing bacteria, as the parent strain, to a mutation process.

Suitable parent strains include, for example, bacteria belonging to *Corynebacterium thermoaminogenes* which are described in Japanese Patent Applicant Laid-Open No. 63-240779 and which are isolated from nature.

There is no particular difficulty in collecting the L-lysine-producing mutant after subjecting the parent strain to a mutation process, but a conventionally known method for collecting a chemical-resistant mutant can be used. For example, the parent strain, which has been subjected to a mutation process with N-methyl N'-nitro-N-nitrosoguanidine (250 ug/ml, 30° C., 30 minutes), or the like, is inoculated on an ordinary agar plate medium containing 1 to 2 g/dl of AEC in which the parent strain cannot be grown, and cultured at 40° C. or higher, e.g., 43° C. The resulting colony is collected and the desired mutant obtained.

Examples of the thus collected L-lysine-producing mutant include the following: *Corynebacterium thermoaminogenes* AJ 12521, *Corynebacterium thermoaminogenes* AJ 12522, *Corynebacterium thermoaminogenes* AJ 12523, and *Corynebacterium thermoaminogenes* AJ 12524. The bacteriological properties of these mutants are shown in Tables 1, 1 through 6.

*Corynebacterium thermoaminogenes* AJ 12308 and AJ 12309 which are parent strains, have been internationally deposited in the Fermentation Research Institute of the Agency of Industrial Science and Technology of Japan under Accession Nos. FERM BP-1540 and FERM BP-1541, respectively. Furthermore, the mutants *Corynebacterium thermoaminogenes* AJ 12521, AJ 12522, AJ 12523, and AJ 12524 have also been internationally deposited in the Fermentation Research Institute of the Agency of Industrial Science and Technology of Japan under Accession Nos. FERM BP-3304, FERM BP-3305, FERM BP-3306 and FERM BP-3307, respectively.

TABLE 1-1

| | Parent Strain AJ 12308 FERM BP-1540 | Mutant AJ 12521 FERM BP-3304 | Mutant AJ 12522 FERM BP-3305 | Parent Strain AJ 12309 FERM BP-1541 | Mutant AJ 12523 FERM BP-3306 | Mutant AJ 12524 FERM BP-3307 |
|---|---|---|---|---|---|---|
| Shape: | | | | | | |
| (1) Shape and size of cell | Rod of 0.7–1.0 × 1.0–4.0 μm; Cell edges are rounded. V-shaped configuration based on snapping division is noted. | Rod of 0.7–1.0 × 1.0–4.0 μm; Cell edges are rounded. V-shaped configuration based on snapping division is noted. | Rod of 0.7–1.0 × 1.0–4.0 μm; Cell edges are rounded. V-shaped configuration based on snapping division is noted. | Rod of 0.7–1.0 × 1.0–4.0 μm; Cell edges are rounded. V-shaped configuration based on snapping division is noted. | Rod of 0.7–1.0 × 1.0–4.0 μm; Cell edges are rounded. V-shaped configuration based on snapping division is noted. | Rod of 0.7–1.0 × 1.0–4.0 μm; Cell edges are rounded. V-shaped configuration based on snapping division is noted. |
| (2) Polymorphism | No polymorphism is noted but depending on the phase of incubation, long rod cells, mast cells and premature cells are rarely noted. | No polymorphism is noted but depending on the phase of incubation, long rod cells, mast cells and premature cells are rarely noted. | No polymorphism is noted but depending on the phase of incubation, long rod cells, mast cells and premature cells are rarely noted. | No polymorphism is noted but depending on the phase of incubation, long rod cells, mast cells and premature cells are rarely noted. | No polymorphism is noted but depending on the phase of incubation, long rod cells, mast cells and premature cells are rarely noted. | No polymorphism is noted but depending on the phase of incubation, long rod cells, mast cells and premature cells are rarely noted. |
| (3) Motility | None | None | None | None | None | None |
| (4) Spore | None | None | None | None | None | None |
| (5) Gram Staining | Positive | Positive | Positive | Positive | Positive | Positive |
| (6) Antacid | Negative | Negative | Negative | Negative | Negative | Negative |

TABLE 1-2

| | Parent Strain AJ 12308 | Mutant AJ 12521 | Mutant AJ 12522 | Parent Strain AJ 12309 | Mutant AJ 12523 | Mutant AJ 12524 |
|---|---|---|---|---|---|---|
| Physiological properties: | | | | | | |
| (1) Bouillon agar plate culture | Abundant or moderate growth; Colonies are circular, smooth, entire convex, glossy, opaque or translucent, dull yellow butyrous. | Abundant or moderate growth; Colonies are circular, smooth, entire convex, glossy, opaque or translucent, dull yellow butyrous. | Abundant or moderate growth; Colonies are circular, smooth, entire convex, glossy, opaque or translucent, dull yellow butyrous. | Abundant or moderate growth; Colonies are circular, smooth, entire convex, glossy, opaque or translucent, dull yellow butyrous. | Abundant or moderate growth; Colonies are circular, smooth, entire convex, glossy, opaque or translucent, dull yellow butyrous. | Abundant or moderate growth; Colonies are circular, smooth, entire convex, glossy, opaque or translucent, dull yellow butyrous. |
| (2) Bouillon agar slant culture | Abundant or moderate growth; filiform, glossy, dull yellow | Abundant or moderate growth; filiform, glossy, dull yellow | Abundant or moderate growth; filiform, glossy, dull yellow | Abundant or moderate growth; filiform, glossy, dull yellow | Abundant or moderate growth; filiform, glossy, dull yellow | Abundant or moderate growth; filiform, glossy, dull yellow |
| (3) Bouillon liquid culture | Moderate growth; colony becomes turbid almost uniformly but some cells precipitate. | Moderate growth; colony becomes turbid almost uniformly but some cells precipitate. | Moderate growth; colony becomes turbid almost uniformly but some cells precipitate. | Moderate growth; colony becomes turbid almost uniformly but some cells precipitate. | Moderate growth; colony becomes turbid almost uniformly but some cells precipitate. | Moderate growth; colony becomes turbid almost uniformly but some cells precipitate. |
| (4) Bouillon gelatin stab culture | Moderate growth; no gelatin is liquefied. | Moderate growth; no gelatin is liquefied. | Moderate growth; no gelatin is liquefied. | Moderate growth; no gelatin is liquefied. | Moderate growth; no gelatin is liquefied. | Moderate growth; no gelatin is liquefied. |
| (5) Litmus milk | Slightly weakly alkaline; Neither liquefaction nor solidification is noted. | Slightly weakly alkaline; Neither liquefaction nor solidification is noted. | Slightly weakly alkaline; Neither liquefaction nor solidification is noted. | Slightly weakly alkaline; Neither liquefaction nor solidification is noted. | Slightly weakly alkaline; Neither liquefaction nor solidification is noted. | Slightly weakly alkaline; Neither liquefaction nor solidification is noted. |

TABLE 1-3

|  | Parent Strain | Mutant | | Parent Strain | Mutant | |
|---|---|---|---|---|---|---|
|  | AJ 12308 | AJ 12521 | AJ 12522 | AJ 12309 | AJ 12523 | AJ 12524 |
| Physiological properties: | | | | | | |
| (1) Reduction of nitrate | Positive | Positive | Positive | Positive | Positive | Positive |
| (2) Denitration | Negative | Negative | Negative | Negative | Negative | Negative |
| (3) MR test | Negative or slight positive | Negative or slight positive | Negative or slight positive | Negative or slight positive | Negative or slight positive | Negative or slight positive |
| (4) VP test | Positive | Positive | Positive | Positive | Positive | Positive |
| (5) Indole formation | Negative | Negative | Negative | Negative | Negative | Negative |
| (6) Formation of hydrogen sulfide | Positive | Positive | Positive | Positive | Positive | Positive |
| (7) Starch hydrolysis | Negative | Negative | Negative | Negative | Negative | Negative |
| (8) Utilization of citrate | Does not grow in Koser medium but grows in Christensen medium; renders medium alkaline. | Does not grow in Koser medium but grows in Christensen medium; renders medium alkaline. | Does not grow in Koser medium but grows in Christensen medium; renders medium alkaline. | Does not grow in Koser medium but grows in Christensen medium; renders medium alkaline. | Does not grow in Koser medium but grows in Christensen medium; renders medium alkaline. | Does not grow in Koser medium but grows in Christensen medium; renders medium alkaline. |
| (9) Utilization of inorganic nitrogen | Does not utilize nitrates but utilizes ammonium salts. | Does not utilize nitrates but utilizes ammonium salts. | Does not utilize nitrates but utilizes ammonium salts. | Does not utilize nitrates but utilizes ammonium salts. | Does not utilize nitrates but utilizes ammonium salts. | Does not utilize nitrates but utilizes ammonium salts. |

TABLE 1-5

|  | Parent Strain | Mutant | | Parent Strain | Mutant | |
|---|---|---|---|---|---|---|
|  | AJ 12308 | AJ 12521 | AJ 12522 | AJ 12309 | AJ 12523 | AJ 12524 |
| (17) Acid formation from sugar: | | | | | | |
| 1 L-Arabinose | Negative | Negative | Negative | Negative | Negative | Negative |
| 2 D-Xylose | Negative | Negative | Negative | Negative | Negative | Negative |
| 3 D-Glucose | Positive | Positive | Positive | Positive | Positive | Positive |
| 4 D-Mannose | Positive | Positive | Positive | Positive | Positive | Positive |
| 5 D-Fructose | Positive | Positive | Positive | Positive | Positive | Positive |
| 6 D-Galactose | Negative | Negative | Negative | Negative | Negative | Negative |
| 7 Maltose | Positive | Positive | Positive | Positive | Positive | Positive |
| 8 Sucrose | Positive | Positive | Positive | Positive | Positive | Positive |
| 9 Lactose | Negative | Negative | Negative | Negative | Negative | Negative |
| 10 Trehalose | Negative | Negative | Negative | Negative | Negative | Negative |
| 11 D-Sorbitol | Negative | Negative | Negative | Negative | Negative | Negative |
| 12 D-Mannitol | Negative | Negative | Negative | Negative | Negative | Negative |
| 13 Inositol | Negative | Negative | Negative | Negative | Negative | Negative |
| 14 Glycerine | Negative | Negative | Negative | Negative | Negative | Negative |
| 15 Starch | Negative | Negative | Negative | Negative | Negative | Negative |

TABLE 1-6

|  | Parent Strain | Mutant | | Parent Strain | Mutant | |
|---|---|---|---|---|---|---|
|  | AJ 12308 | AJ 12521 | AJ 12522 | AJ 12309 | AJ 12523 | AJ 12524 |
| Other characterisitcs: | | | | | | |
| (1) Temperature resistance | By capillary method in skimmed milk: Alive ab 60° C., 10 mins. Dead ab 65° C., 10 mins. | By capillary method in skimmed milk: Alive ab 60° C., 10 mins. Dead ab 65° C., 10 mins. | By capillary method in skimmed milk: Alive ab 60° C., 10 mins. Dead ab 65° C., 10 mins. | By capillary method in skimmed milk: Alive ab 60° C., 10 mins. Dead ab 65° C., 10 mins. | By capillary method in skimmed milk: Alive ab 60° C., 10 mins. Dead ab 65° C., 10 mins. | By capillary method in skimmed milk: Alive ab 60° C., 10 mins. Dead ab 65° C., 10 mins. |
| (2) Sodium chloride resistance | Grows in medium containing 5% saline. | Grows in medium containing 5% saline. | Grows in medium containing 5% saline. | Grows in medium containing 5% saline. | Grows in medium containing 5% saline. | Grows in medium containing 5% saline. |
| (3) Nutrient auxotrophy | Requires biotin for growth. | Requires biotin for growth. | Requires biotin for growth. | Requires biotin for growth. | Requires biotin for growth. | Requires biotin for growth. |
| (4) Nucleotide composition of DNA (Tm method) | 60.2% GC | 60.2% GC | 60.2% GC | 59.5% GC | 59.5% GC | 59.5% GC |
| (5) Dibasic amino acid contained in cell wall | Meso-diaminopimelic acid | Meso-diaminopimelic acid | Meso-diaminopimelic acid | Meso-diaminopimelic acid | Meso-diaminopimelic acid | Meso-diaminopimelic acid |
| (6) Source | Fruit | — | — | Vegetable | — | — |

TABLE 1-4

|  | | Parent Strain AJ 12308 | Mutant AJ 12521 | Mutant AJ 12522 | Parent Strain AJ 12309 | Mutant AJ 12523 | Mutant AJ 12524 |
|---|---|---|---|---|---|---|---|
| (10) | Pigment formation | No pigment is formed extracellularly. | No pigment is formed extracellularly. | No pigment is formed extracellularly. | No pigment is formed extracellularly. | No pigment is formed extracellularly. | No pigment is formed extracellularly. |
| (11) | Urease test | Negative or slightly positive | Negative or slightly positive | Negative or slightly positive | Negative or slightly positive | Negative or slightly positive | Negative or slightly positive |
| (12) | Oxidase | Negative | Negative | Negative | Negative | Negative | Negative |
| (13) | Catalase | Positive | Positive | Positive | Positive | Positive | Positive |
| (14) | Growth range | Grows well at Ph 7–8.5; grows well at 35–45° C.; grows slightly at 46–50° C. | Grows well at Ph 7–8.5; grows well at 35–45° C.; grows slightly at 46–50° C. | Grows well at Ph 7–8.5; grows well at 35–45° C.; grows slightly at 46–50° C. | Grows well at Ph 7–8.5; grows well at 35–45° C.; grows slightly at 46–50° C. | Grows well at Ph 7–8.5; grows well at 35–45° C.; grows slightly at 46–50° C. | Grows well at Ph 7–8.5; grows well at 35–45° C.; grows slightly at 46–50° C. |
| (15) | Behavior to oxygen | Aerobic or facultative anerobic | Aerobic or facultative anerobic | Aerobic or facultative anerobic | Aerobic or facultative anerobic | Aerobic or facultative anerobic | Aerobic or facultative anerobic |
| (16) | O-F test (glucose) | Grows fermentatively to form acid. | Grows fermentatively to form acid. | Grows fermentatively to form acid. | Grows fermentatively to form acid. | Grows fermentatively to form acid. | Grows fermentatively to form acid. |

The medium used for producing and accumulating L-lysine using the present L-lysine-producing mutant, may be any conventional known medium for producing L-lysine. Conventional media containing carbon sources, nitrogen sources, inorganic salts, and, if necessary, other organic trace nutrients which the microorganism uses, can be used. Any carbon source may be used so long as the mutant used can use the same. Examples of the carbon sources include glucose, sucrose, maltose, starch hydrolysates containing them, sugars such as molasses, and the like; alcohols such as ethanol, propanol and the like; organic acids such as acetic acid, propionic acid, and the like. In addition, normal paraffin, and the like may also be used singly or in combination with other carbon sources, depending on the strain. As nitrogen sources, inorganic and organic nitrogen sources may be used including ammonium salts such as ammonium acetate, ammonium chloride, ammonium phosphate, and the like., nitrates, urea, ammonia, and furthermore, meat extract, and the like. Suitable inorganic salts include $KH_2PO_4$, $MgSO_4$, $FeSO_4$, $MnSO_4$ and the like which are ordinarily used. Suitable organic trace nutrients include vitamins, fatty acids and nucleic acids, and peptone, casamino acid, yeast extract or protein hydrolysate containing them.

Incubation is preferably carried out under aerobic conditions. By carrying out shake culture or aerial spinner culture for 2 to 4 days, and adjusting the pH of the medium to a range from 5 to 9, preferably 7 to 8.5 at the growth temperature of the bacteria used, i.e., about 25° to about 50° C., preferably about 35° to about 45° C. in order to achieve high L-lysine productivity, L-lysine can be produced and accumulated in the culture medium in a marked quantity.

Conventional methods for collecting L-lysine from the culture medium can be used. For example, L-lysine may be recovered by the conventional ion exchange resin method, crystallization, or the like in an appropriate combination.

As described above, the temperature for fermentation of L-lysine in accordance with the present invention is at the growth temperature of bacteria used, namely about 25° to about 50° C., preferably 35° to 45° C. at which L-lysine productivity increases. Examples 2 and 3 actually demonstrate that L-lysine was formed and accumulated in a remarkable quantity, by regulating the fermentation temperature at 43° C. on a laboratory scale.

Based on the experimental results, the cooling load for removing heat generated by fermentation on a commercial scale was calculated by trial. In the event that fermentation of L-lysine was performed using a fermentation tank having a volume of, e.g., 200 kiloliters, the cooling load for maintaining the optimum fermentation temperature, e.g., 30° C., for L-lysine-producing bacteria was 30 millionkilocalories per batch, whereas in the present invention the cooling load for maintaining the fermentation temperature not exceeding 43° C. was 3 million kilocalories per batch, when the L-lysine-producing mutant of the present invention was used. As is clear from the above data, the cooling load can be reduced by 90% by the method of the present invention.

Having now generally described the invention, it will be apparent to one of ordinary skill in the art that many changes and modifications can be made thereto without departing from the spirit or scope of the invention as set forth herein.

EXAMPLE 1

(harvest of mutant)

After *Corynebacterium thermoaminogenes* AJ 12308 was treated with N-methyl-N-nitro-N-nitrosoguanidine (250 μg/ml, 30° C., 30 minutes) in a conventional manner, incubation was conducted at 43° C. in a medium obtained by supplementing the minimum medium below with 1.5 g/dl of AEC. Colonies grown at 43° C. in the medium were harvested.

| Composition of minimum medium: | | |
|---|---|---|
| Glucose | 2.0 | g/dl |
| Urea | 0.25 | g/dl |
| Ammonium sulfate | 1.0 | g/dl |
| $KH_2PO_4$ | 0.1 | g/dl |
| $MgSO_4.7H_2O$ | 0.04 | g/dl |
| $FeSO_4.7H_2O$ | 1.0 | mg/dl |
| L-Alanine | 50 | mg/dl |
| Nicotinamide | 0.5 | mg/dl |
| $MnSO_4.4H_2O$ | 1.0 | mg/dl |
| Biotin | 5.0 | μg/dl |
| Thiamine hydrochloride | 10 | μg/dl |
| NaCl | 5 | mg/dl |
| pH 7.2 | | |

Among the mutants thus obtained, AJ 12521 and AJ 12522 were harvested as mutants having excellent L-lysine productivity.

In a similar manner, AJ 12523 and AJ 12524 were harvested using *Corynebacterium thermoaminogenes* AJ 12309 as the parent strain.

The four mutants thus obtained were previously grown on glucose-bouillon agar medium at 43° C. One platinum loop aliquotos were inoculated respectively on 20 ml of sterile medium charged into a shaking flask of 500 ml volume and having the following composition.

| Composition of medium: | | |
|---|---|---|
| Beat molasses | 10 | g/dl |
| Ammonium sulfate | 5 | g/dl |
| KH$_2$PO$_4$ | 0.1 | g/dl |
| MgSO$_4$.7H$_2$O | 40 | mg/dl |
| Biotin | 50 | μg/dl |
| Calcium carbonate (separately sterilized and added) | 5 | g/dl |
| pH 7.0 | | |

These mutants were cultured at 43° C. for 72 hours. Lysine was accumulated as shown in Table 2.

TABLE 2

| Strain | Concentration of L-lysine accumulated (g/dl) |
|---|---|
| AJ 12521 | 3.2 |
| AJ 12522 | 2.9 |
| AJ 12523 | 2.8 |
| AJ 12524 | 3.0 |

EXAMPLE 2

In a shaking 500 ml volume flask, 20 ml of aqueous medium having the following composition was separately charged followed by sterilization at 110° C. for 10 minutes with steam.

| Composition of medium: | | |
|---|---|---|
| Glucose | 10 | g/dl |
| Ammonium sulfate | 4.5 | g/dl |
| KH$_2$PO$_4$ | 0.1 | g/dl |
| MgSO$_4$.7H$_2$O | 0.04 | g/dl |
| FeSO$_4$.7H$_2$O | 1.0 | mg/dl |
| MnSO$_4$.4H$_2$O | 1.0 | mg/dl |
| Biotin | 5.0 | μg/dl |
| Thiamine hydrochloride | 20 | μg/dl |
| Concentrate of soybean protein hydrolysate with hydrochloric acid (total nitrogen, 7%) | 1.5 | ml/dl |
| Calcium carbonate (separately sterilized and added) | 5 | g/ml |
| pH 7.0 | | |

One platinum loop of *Corynebacterium thermoaminogenes* AJ 12521 which had been previously grown on a glucose bouillon slant was inoculated on the thus prepared medium charged in a flask. Shaking culture was conducted at 43° C. for 72 hours.

The amount of L-lysine produced in the medium after culturing for 72 hours was colorimetrically determined using the ninhydrin reaction. The results indicate that L-lysine was produced in an amount of 3.0 g/dl.

Furthermore, solutions corresponding to 50 flasks cultured in a similar manner which completed incubation were collected and the cells and calcium salt were removed by centrifugation. About 1 liter of the thus obtained supernatant was passed through a strongly acidic ion exchange resin (AMBERLITE" IR-120 (OH type)) to adsorb L-lysine thereonto. The adsorbed L-lysine was eluted with 3% ammonia water and the eluate was concentrated under reduced pressure. After hydrochloric acid was added to the concentrate, the mixture was cooled and L-lysine was precipitated as L-lysine hydrochloride dihydrate to give 26.5 g of crystals.

EXAMPLE 3

One platinum loop each of *Corynebacterium thermoaminogenes* AJ 12523 and the parent strain AJ 12309 was taken from the slant and inoculated on 50 ml of the aqueous seed culture medium described below. Aerial spinner culturing was performed at 43° C. for 18 hours to prepare a seed culture medium.

| Composition of seed culture medium: | | |
|---|---|---|
| Glucose | 1.5 | g/dl |
| Ammonium sulfate | 0.3 | g/dl |
| Urea | 0.1 | g/dl |
| KH$_2$PO$_4$ | 0.1 | g/dl |
| MgSO$_4$.7H$_2$O | 0.04 | g/dl |
| FeSO$_4$.7H$_2$O | 1.0 | mg/dl |
| MnSO$_4$.4H$_2$O | 1.0 | mg/dl |
| Biotin | 5.0 | μg/dl |
| Thiamine hydrochloride | 20 | μg/dl |
| Concentrate of soybean protein hydrolysate with hydrochloric acid (total nitrogen, 7%) | 2.0 | ml/dl |
| pH 7.5 | | |

On the other hand, 300 ml aliquots of aqueous medium for main fermentation having the composition described below were each charged into a glass-made jar fermenter of 1 liter volume and sterilized in a conventional manner.

Each medium was inoculated with 15 ml of the seed culture medium and aerial spinner culturing was initiated at 43° C.

| Composition of medium for main fermentation: | | |
|---|---|---|
| Glucose | 2.0 | g/dl |
| Ammonium sulfate | 0.5 | g/dl |
| Urea | 0.2 | g/dl |
| KH$_2$PO$_4$ | 0.1 | g/dl |
| MgSO$_4$.7H$_2$O | 0.04 | g/dl |
| FeSO$_4$.7H$_2$O | 1.0 | mg/dl |
| MnSO$_4$.4H$_2$O | 1.0 | mg/dl |
| Biotin | 5.0 | μg/dl |
| Thiamine hydrochloride | 50 | μg/dl |
| Nicotinamide | 1.0 | mg/dl |
| Concentrate of soybean protein hydrolysate with hydrochloric acid (total nitrogen, 7%) | 3.0 | ml/dl |
| pH 7.2 | | |

A mixture of acetic acid and ammonium acetate (molar ratio of acetic acid:ammonium acetate in the mixture was 1:0.25; concentration of acetic acid in the mixture was 60%) was added to the culture medium to maintain the pH of the medium between 7.2 and 8.0. Incubation was performed at 43° C. for 55 hours.

The results are shown in Table 3.

TABLE 3

| Strain Used | Amount of L-Lysine Accumulated (g/dl) |
|---|---|
| AJ 12523 | 3.2 |
| AJ 12309 (parent) | 0.03 |

From 300 ml of the solution obtained after completion of fermentation of AJ 12323, 1.0 g of L-lysine hydrochloride dihydrate was obtained as crystals in a manner similar to Example 2.

EXAMPLE 4

In a shaking flask of 500 ml volume, 20 ml of the same medium as used in Example 2 was charged followed by sterilization at 110° C. for 10 minutes with steam. One platinum loop of *Corynebacterium thermoaminogenes* AJ 12524, which had been previously grown on glucose-bouillon slant, was inoculated on the medium followed by shaking culturing at 43° C. for 50 hours.

After 0.2 ml of the culture medium was charged into a glass-made jar fermenter, 5 ml of cooled physiological saline was added thereto. After stirring, the mixture was centrifuged at 4500 rpm for 10 minutes and the supernatant was discharged.

A mixture of 1.5 ml of 0.2 M phosphate buffer (pH 7.5) and 1.5 ml of the reaction solution described below was added and the mixture was stirred. The cells were suspended followed by a shaking reaction (120 rpm) at 43° C. for 2 hours.

| Reaction solution: | | |
|---|---|---|
| Glucose | 1 | g/dl |
| $(NH_4)_2SO_4$ | 0.4 | g/dl |
| $MgSO_4.7H_2O$ | 0.04 | g/dl |
| Biotin | 500 | μg/dl |
| pH 7.5 | | |

Thereafter, centrifugation (4500 rpm, 10 minutes) was carried out and the concentration of L-lysine in the supernatant was analyzed by liquid chromatography. The results showed that 0.2 g/dl of L-lysine had accumulated.

The present invention provides a method for producing L-lysine on a industrial scale in which the cooling load for eliminating heat generated upon fermentation is reduced. Further, the method requires no amino acid nutrients and can be practically used.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for producing L-lysine by fermentation comprising:
   culturing in a nutrient medium containing assimilable sources of carbon, nitrogen, and inorganic salts a strain of *Corynebacterium thermoaminogenes* which is capable of growing at 40° C. or higher and is resistant to S-(2-aminoethyl)-L-cysteine under conditions effective for the production of L-lysine wherein said strain is selected from the group consisting of *Corynebacterium thermoaminogenes* AJ 12521, FERM BP-3304, *Corynebacterium thermoaminogenes* AJ 12522, FERM BP-3305, *Corynebacterium thermoaminogenes* AJ 12523, FERM BP-3306, *Corynebacterium thermoaminogenes* AJ 12524, FERM BP-3307; and
   collecting L-lysine from the culture medium.

2. The method of claim 1, wherein culturing is conducted at a temperature of 25° to about 50° C.

3. The method of claim 2, wherein the culturing temperature ranges from 35° to 45° C.

4. The method of claim 1, wherein culturing is conducted at a pH of 5 to 9.

5. The method of claim 4, wherein culturing is conducted at a pH of 7 to 8.5.

* * * * *

UNITED STATES PATENT AND TRADEMARK OFFICE
CERTIFICATE OF CORRECTION

PATENT NO. : 5,250,423
DATED : October 5, 1993
INVENTOR(S) : Yutaka Murakami, et al.

It is certified that error appears in the above-indentified patent and that said Letters Patent is hereby corrected as shown below:

Column 1, line 43, "No. 85-231" should read --No. 85-1231--;
  line 58, "(37° to 45°C.)." should read --(37° to 45°C.),--.

Column 2, line 66, "(250 ug/ml, 30° C., 30 minutes)," should read --(250 µg/ml, 30° C., 30 minutes),--.

Column 10, line 2 "(AMBERLITE" IR-120 (OH type))" should read --("AMBERLITE" IR-120 (OH type))--.

Signed and Sealed this

Twenty-fourth Day of January, 1995

Attest:

BRUCE LEHMAN

*Attesting Officer*    *Commissioner of Patents and Trademarks*